US00PP07892P

United States Patent [19]

van Andel

[11] Patent Number: Plant 7,892

[45] Date of Patent: Jun. 23, 1992

[54] CARNATION NAMED STAWIZA

[75] Inventor: Jacob van Andel, Aalsmeer, Netherlands

[73] Assignee: Vann Staaveren B.V., Aalsmeer, Netherlands

[21] Appl. No.: 604,530

[22] Filed: Oct. 29, 1990

[51] Int. Cl.[5] ..... A01H 5/00

[52] U.S. Cl. ..... Plt./70

[58] Field of Search ..... Plt./70

*Primary Examiner*—James R. Feyrer

*Attorney, Agent, or Firm*—Charles W. Rummler

[57] ABSTRACT

A new and original carnation cultivar particularly distinguished by its enormous white blossoms, which are produced continuously in Spring, Summer, Fall, and Winter. The plant has a strong and vigorous growth habit and a height of about 120 cm.

1 Drawing Sheet

BACKGROUND OF THE NEW PLANT

This new carnation cultivar originated as a Hybrid Seedling developed by me in 1985 at our nursery in Aalsmeer, Holland by crossing two varieties selected from our collection of carnations maintained for breeding purposes at Aalsmeer. This particular seedling was selected for propagation because of its white coloration, the size of the flowers, and the overall high quality of its growth habit. Asexual propagation of this selected plant was done by means of cuttings under my direction at Aalsmeer and propagation of this new plant by cuttings continued from generation to generation to determine whether the novel characteristics of the selected seedling would hold true, so that its homogeneity could be assured.

This proved to be successful and this new carnation variety is now being propagated at Aalsmeer.

DESCRIPTION OF THE DRAWING

My new carnation cultivar is illustrated by the accompanying photographic drawing, which shows blooming portions of flower stems with the flowers shown in full development, the color rendition being as nearly true to that herein specified as is reasonably possible to obtain by professional photographic procedures.

DESCRIPTION OF THE NEW PLANT

The following is a detailed description of my new carnation variety based upon observation of plants grown in greenhouse as well as outdoors at Aalsmeer and blooming during the current year. The color designations stated herein are according to the R.H.S. Colour Chart published by The Royal Horticultural Society of London, England.

THE PLANT

Origin: Seedling.

Parentage:

*Seed parent.*—84272-1C (unpatented).

*Pollen parent.*—85460-1G (unpatented).

Classification:

*Botanic.*—*Dianthus caryophyllus.*

*Commercial.*—Standard carnation.

Form: Tall, vigorous bush.

Height: 120 cm, in average.

Main stem:

*Length.*—100 cm.

*Growth.*—Vigorous and strong.

*Branching character.*—One side shoot at each node.

Foliage:

*Number of leaves.*—Varies with season and the amount of daylight.

*Leaf size.*—14 cm × 1.3 cm at the fifth node.

*Leaf shape.*—Pointed and curled. Margins: Entire. Texture: Leathery. Color: Both upper and under side are gray-green.

THE BUD

Size: Medium.

*Diameter.*—Averaging about 2.5 cm.

*Length.*—Averaging anout 3 cm.

Shape: Ovoid.

Calyx:

*Shape.*—Funnel-shaped.

*Size.*—Averaging about 2 cm in width and 3 cm in length.

*Splitting.*—The calyx does not split.

*Aspect.*—Smooth.

Flower stem:

*Character.*—Sturdy and erect.

*Color.*—Gray-green.

THE FLOWER

Blooming habit: Continuous, blooming the year around.

Size of flower: Very large.

*Diameter.*—Averaging about 9 cm.

*Depth.*—Averaging about 4 cm.

Borne: Singly.

Shape when first opening: High center.

*When mature.*—Low dome.

Petalage:

*Arrangement.*—Imbricated.

*Form/Shape.*—Ovate.

*Margin type.*—Deeply serrate.

*Texture.*—Soft.

*Appearance.*—Velvety.

*Number of petals.*—Approximately 20-25.

*Color.*—Both outer and inside petals: Body: 155 D. Base: 155 D. Reverse Side: 155 D.

Flower stem:

*Length.*—80-100 cm.

*Character.*—Strong and upright

Discoloration:

*After full bloom.*—No discoloration.

Persistence: The flowers hang on and dry.
Disease resistance: Resistant to *Fusarium Oxysporum.*
Lasting quality: Averaging about 10 days as a cut flower and 18 days on the plant.
Fragrance: Slight.

REPRODUCTIVE ORGANS

Stamens:

*Number.*—Few.

*Arrangement.*—Petaloid. Anthers: Size: Small.

*Color.*—Yellow-brown. Filaments: Length: About 35 mm, in average. Color: White. Pollen: Color: White.

Pistils:

*Number.*—1.

*Styles.*—Length: About 30 mm. Color: White.

*Stigmas.*—Color: Greenish-white.

Characteristics of ovaries: Conical.

FRUIT

Fertility: The fruit is fertile.
Shape: Conical.
Color at maturity: Light brown.

I claim:

1. The new and distinctive carnation cultivar, substantially as herein shown and described, particularly characterized by the white coloration of its large continuously blooming flowers, which are borne singly on strong, upright stems.

* * * * *

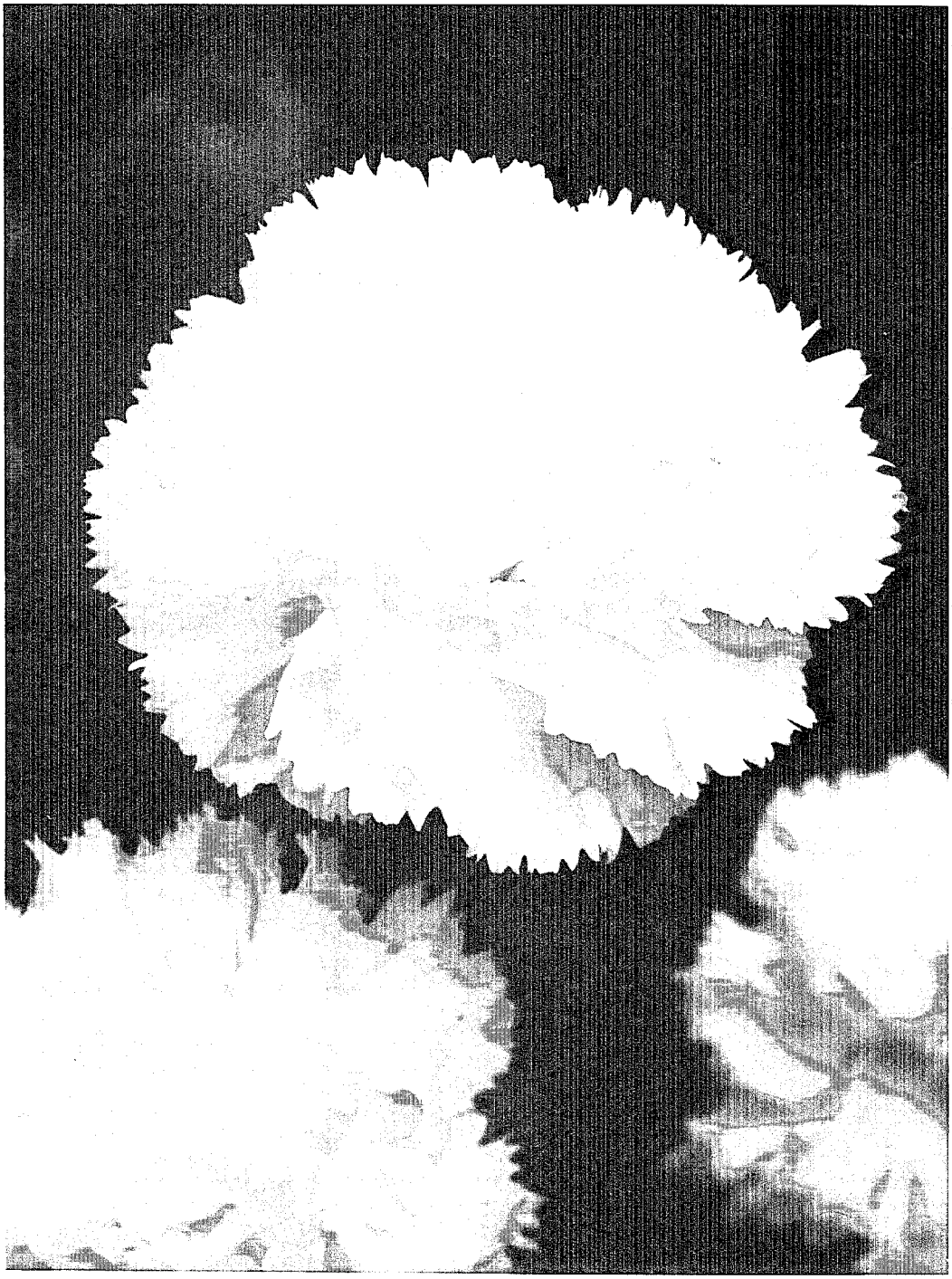

UNITED STATES PATENT AND TRADEMARK OFFICE

CERTIFICATE OF CORRECTION

PATENT NO. : Plant 7,892

DATED : June 23, 1992

INVENTOR(S) : JACOB VAN ANDEL

It is certified that error appears in the above-identified patent and that said Letters Patent is hereby corrected as shown below:

On the title page: Item [73]

Assignee: : delete "Vann" and insert --van-- col.2, 1.15, delete "anout" and insert --about--.

Signed and Sealed this

Third Day of August, 1993

*Attest:*

Michael K. Kirk

MICHAEL K. KIRK

*Attesting Officer*

*Acting Commissioner of Patents and Trademarks*